(12) United States Patent
Drechsler et al.

(10) Patent No.: US 11,067,565 B2
(45) Date of Patent: Jul. 20, 2021

(54) DEVICE AND METHOD FOR BIOLOGICAL SAMPLE COLLECTION AND INSPECTION

(71) Applicant: Roche Molecular Systems, Inc., Pleasanton, CA (US)

(72) Inventors: Andreas Drechsler, Baar (CH); Edwin Oosterbroek, Cham (CH); Emad Sarofim, Hagendorn (CH); Heiko Schwertner, Ebikon (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 498 days.

(21) Appl. No.: 15/923,840

(22) Filed: Mar. 16, 2018

(65) Prior Publication Data

US 2018/0209964 A1    Jul. 26, 2018

Related U.S. Application Data

(63) Continuation of application No. 14/325,788, filed on Jul. 8, 2014, now Pat. No. 9,939,429.

(30) Foreign Application Priority Data

Jul. 10, 2013  (EP) .................................... 13175833

(51) Int. Cl.
*G01N 35/00* (2006.01)
*G01N 33/50* (2006.01)
*B01L 3/00* (2006.01)

(52) U.S. Cl.
CPC ...... *G01N 33/5091* (2013.01); *B01L 3/50853* (2013.01); *B01L 3/545* (2013.01); *B01L 2300/02* (2013.01); *G01N 35/00732* (2013.01)

(58) Field of Classification Search
CPC .. B01L 3/5027; B01L 3/5085; B01L 3/50853; B01L 3/54; B01L 3/545; G01N 33/5091; G01N 35/00732
See application file for complete search history.

(56) References Cited

U.S. PATENT DOCUMENTS 6,902,703 B2    6/2005  Marquiss et al.
7,537,735 B2 *  5/2009  Hiemer ............. G01N 35/1011
                                                   422/106
(Continued)

FOREIGN PATENT DOCUMENTS

CN    102985810 A    3/2013
EP       1738828     1/2007
(Continued)

*Primary Examiner* — Jill A Warden
*Assistant Examiner* — Dwayne K Handy
(74) *Attorney, Agent, or Firm* — Maneesh Gupta

(57) ABSTRACT

A device is described including a lid, a collection portion support, and a collection portion with a surface for receiving a biological sample, the lid includes a window and a window holder, the surface defines a first plane, the collection portion includes a first, a second, and a third position markers, each position marker indicates a center point marker, the center points define a second plane that has a line of intersection with the first plane, the device has an interior volume defined partially by the collection portion support, the collection portion, the window, and the window holder, the window allows visual inspection of the position markers, the collection portion support has a fluid inlet and a fluid outlet with a fluid path from the fluid inlet to the fluid outlet via the interior volume.

8 Claims, 15 Drawing Sheets

(56) References Cited

U.S. PATENT DOCUMENTS

| | | |
|---|---|---|
| 9,939,429 B2 | 4/2018 | Drechsler et al. |
| 2001/0048899 A1 | 12/2001 | Marouiss et al. |
| 2005/0118640 A1 | 6/2005 | Kureshy et al. |
| 2008/0056951 A1* | 3/2008 | Angros .................... G01N 1/30 422/400 |
| 2011/0033854 A1 | 2/2011 | Drmanac et al. |
| 2011/0177548 A1 | 7/2011 | Graham et al. |

FOREIGN PATENT DOCUMENTS

| | | |
|---|---|---|
| JP | 2003519784 A | 6/2003 |
| JP | 2005221725 A | 8/2005 |
| JP | 2005527827 A | 9/2005 |
| JP | 2006000052 A | 1/2006 |
| JP | 2011103779 A | 6/2011 |
| JP | 2014090692 A | 5/2014 |
| WO | 01/51207 | 7/2001 |
| WO | 2008/050165 | 5/2008 |

* cited by examiner

US 11,067,565 B2

DEVICE AND METHOD FOR BIOLOGICAL SAMPLE COLLECTION AND INSPECTION

CROSS-REFERENCES TO RELATED APPLICATIONS

The present application claims the benefit of priority under 35 U.S.C. § 119 of EP 13175833.6, filed Jul. 10, 2013, and U.S. application Ser. No. 14/325,788, filed Jul. 8, 2014, the content of which is incorporated by reference herein in its entirety.

FIELD OF THE INVENTION

The present disclosure relates to the field of collection and inspection of biological samples, and in particular to a device, an optical analyzer, and a method of identifying a three-dimensional location in the device for collection and inspection of biological samples.

BACKGROUND OF THE INVENTION

For detecting cancer or other diseases, optical or other systems may be used to scan for abnormal cells. Biological samples containing cells may be placed into a holder or collection device for inspection. International Patent application WO 2008/050165 A1 discloses a cuvette for the optical analysis of urine.

A disadvantage of current devices for holding samples is that once a sample component is identified, it may be difficult to reproducibly locate the sample component again. For example temperature changes can cause dimensional changes in devices for holding sample components.

The present disclosure provides for a device, an optical analyzer, and a method of identifying a three-dimensional location in the device in various embodiments.

SUMMARY OF THE INVENTION

In one embodiment, a device is provided for collection of biological samples, including a lid, a collection portion support, and a collection portion with a surface for receiving a biological sample, wherein the lid includes a window and a window holder, wherein the surface defines a first plane, and wherein the collection portion includes a first position marker, wherein the first position marker indicates a first center point; a second position marker, wherein the second position marker indicates a second center point; and a third position marker, wherein the third position marker indicates a third center point; wherein the first center point, the second center point and the third center point define a second plane, wherein the second plane and the first plane define a line of intersection; wherein the device has an interior volume defined partially by the collection portion support, the collection portion, the window, and the window holder; wherein the interior volume has interior surfaces; wherein the window is operable to allow inspection of the first position marker, the second position marker, and the third position marker; wherein the collection portion support has a fluid inlet and a fluid outlet; wherein the fluid inlet is located at a first side of the device; wherein the fluid outlet is located at a second side of the device; and wherein there is a fluid path from the fluid inlet to the fluid outlet via the interior volume.

In another embodiment, a system is provided to perform an optical analysis of the device as described above; wherein the system includes a location identifier configured to automatically identify the location of the first location marker, the second location marker, and the third location marker; wherein the system is configured to identify the three dimensional location of a biological element on the collection portion relative to the first location marker, the second location marker, and the third location marker.

In another embodiment, a method is provided for identifying a three-dimensional location on a collection portion with a surface for receiving a biological sample; wherein the surface defines a first plane; wherein the collection portion includes a first position marker, wherein the first position marker indicates a first center point, wherein the collection portion further includes a second position marker; wherein the second position marker indicates a second center point, wherein the collection portion further includes a third position marker, wherein the third position marker indicates a third center point, wherein the first center point, the second center point, and the third center point define a second plane, wherein the second plane and the first plane define a line of intersection, wherein the method includes identifying the location of the first position marker, the second position marker, and the third position marker using a location identifier; identifying a biological element on the surface of the collection portion; extrapolating the three-dimensional location of the biological element using the location of the first position marker, the second position marker, and the third position marker.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

DETAILED DESCRIPTION OF THE INVENTION

Figure 1:
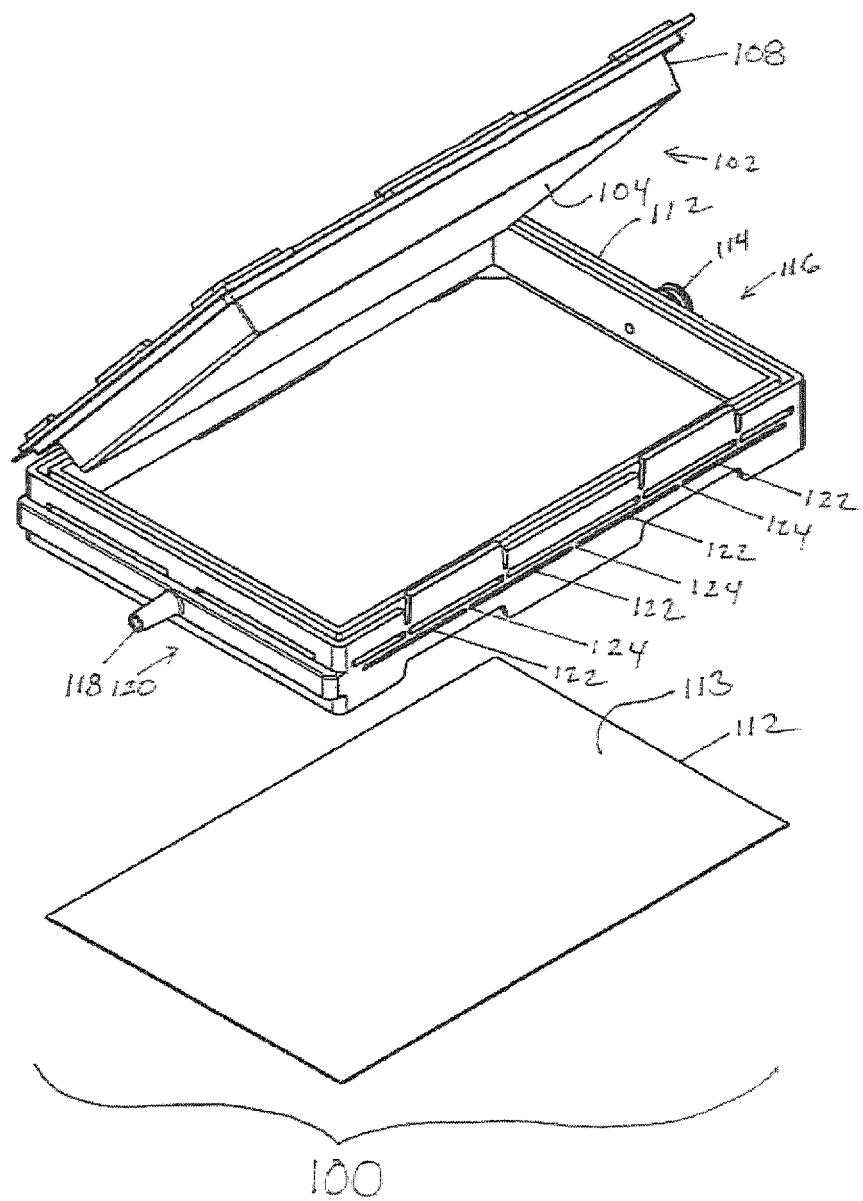
FIG. 1 shows an exploded view of the components which make up an example of a device.

By way of illustration, specific exemplary embodiments in which the invention may be practiced now are described.

In one embodiment, a device is provided including a lid, a collection portion support and a collection portion. The collection portion has a surface for receiving a biological sample. A collection portion as used herein encompasses a sample holder for a biological sample or for a biological cell. The collection portion may for example be, but is not limited to: a microtiter plate, a planar piece of glass, and a planar piece of plastic. The collection portion may be optically transparent.

A biological sample as used herein encompasses a chemical produced by a biological system, a portion of a biological organism, or chemicals or products copied or derived from a biological system. In one particular example the biological sample may be a biological cell or a collection of cells distributed on the surface. In other particular examples, the biological sample comprises one or more cell components such as mitochondria, endoplasmic reticulum, nuclei, liposomes and the like. The lid comprises a window and a window holder. Essentially the window holder may be a frame-like structure which surrounds and supports the window. The surface defines a first plane. In some instances the surface of the collection portion may be flat. In this case the surface for receiving the biological sample defines the first plane in a particular way. In other cases the collection portion may not have a flat surface for receiving the biological sample. However, it may still define a plane. The surface of the biological sample may for instance have a repeating pattern of the surface for receiving the biological sample. The first plane could then be defined as passing through the highest or lowest points of the repeating pattern of the surface. An intermediate point in between the high and low surfaces may also be used to arbitrarily define the first plane. However the first plane would still be parallel to a plane defined by the highest or lowest points.

The collection portion comprises a first position marker. The first position marker indicates a first center point. In some embodiments the first center point may be additionally indicated by a center point marker. In Cartesian coordinates this would be particular x, y, z coordinates relative to the collection portion. The center point of a position marker may be considered to be the location of the position marker.

The first position marker may also comprise other elements which help a machine-readable system to identify the exact location of the center point marker. The collection portion further comprises a second position marker. The second position marker also indicates a second center point. As with the first center point marker, the second center point marker defines a particular location in space. The second position marker may comprise a second center point marker which is positioned at the second center point. The collection portion further comprises a third position marker. The third position marker indicates a third center point which also defines a particular location in space. The third position marker may comprise a third center point marker which indicates or is positioned at the third center point. The first, second and third position markers may each comprise additional elements which helps a machine reading system to identify the location of the particular center point marker.

The first center point, the second center point, and the third center point define a second plane. The second plane and the first plane define a line of intersection. Since the second plane and the first plane define a line of intersection the second plane is therefore tilted with respect to the first plane. Describing the second plane and the first plane having a line of intersection is equivalent to stating that the first position marker, the second position marker, and the third position marker do not lie all on a plane which is parallel to the first plane. As such, with respect to the first plane, the first position marker, the second position marker, and the third position marker define a range of x, y and z coordinates relative to the first plane. The first position marker, the second position marker, and the third position marker may therefore be used to calibrate x, y and z position relative to the first plane.

The device has an interior volume defined partially by the collection portion support, the collection portion, the window, and the window holder. The interior volume has or defines interior surfaces. The window is optically transparent. The window is operable or configured to allow visual inspection of the first position marker, the second position marker, and the third position marker. The collection portion support has a fluid inlet and a fluid outlet. The fluid inlet is located at a first side of the collection portion support. The fluid outlet is located at a second side of the collection portion support. There is a fluid path from the fluid inlet to the fluid outlet via the interior volume.

In some examples the collection portion may also be optically or partially optically transparent. The device may be beneficial because the distribution of the first position marker, the second position marker, and the third position marker within the collection portion enable a machine-readable system to define coordinates in terms of the collection portion.

Known systems may define the coordinates relative to collection portion support. In contrast, embodiments which may define coordinates in terms of the collection portion itself may be beneficial because it may allow for more repeatable determination of a particular location. For instance an optical inspection system may go through and identify the location of the position markers. Then the optical analyzer may go through and identify particular types of cells. The device may be removed from a system and put into another system which is used to remove the cells for a culture or for further inspection. A change in temperature could cause the dimensions of the device to change or the collection portion may shift within the collection portion support causing an error in the location. Putting the position markers within or attached to the collection portion enables identification of coordinates that are in terms of the actual device supporting the biological sample or cells. The position markers may be machine-readable to the location of the center points. They allow a machine-readable system to define a three-dimensional space which may be repeatably determined.

In some examples the position markers may all be embedded within the collection portion. In other embodiments one or two of the position markers is on a surface.

In another embodiment the collection portion support has multiple vents from an outside surface of the collection portion to support the interior volume. This may be beneficial because the vents allow air or other gas to directly reach the interior volume. This may be particularly beneficial when one tries to open the lid. The vents make it easier to remove the lid without disturbing any cells or biological sample which are sitting on the surface for receiving the biological sample.

In another embodiment the multiple vents are operable or configured to be sealed and unsealed. For instance the multiple vents may be closed off by a plug or other movable mechanical system which is operable or configured for either opening or sealing the multiple vents. Being able to seal the multiple vents may be beneficial because it prevents the fluid from the fluid inlet from exiting through the multiple vents. When it is desired to open the lid then the multiple vents can simply be opened and the lid may be easily removed.

In another embodiment the interior surfaces of the collection portion and the window holder are hydrophobic. In some applications this may be beneficial because it reduces the surface tension between the collection portion and the window holder and may make it easier to remove the lid in some cases without disturbing the biological sample or cells within the inner volume.

In another embodiment the first position marker further comprises a first linear indicator. The first linear indicator defines a first line through the first center point. The first position marker comprises a second linear indicator. The second linear indicator defines a second line through the first center point. The first line and the second line are perpendicular. The second position marker comprises a third linear indicator. The third linear indicator defines a third line through the second center point. The second position marker comprises a fourth linear indicator. The fourth linear indicator defines a fourth line through the second center point. The third line and the fourth line are perpendicular. The third position marker further comprises a fifth linear indicator. The fifth linear indicator defines a fifth line through the third center point. The third position marker comprises a sixth linear indicator. The sixth linear indicator defines the sixth line through the third center point. The fifth line and the sixth line are perpendicular. This embodiment may be beneficial because the linear indicators may help a position marker to have its location more easily machine-readable.

In another embodiment the first line and the second line define a third plane that is co-planar or parallel to the first plane. The first line and the third line intersect at an angle of 45 degrees when the third line is projected into the third plane. The third line and the fourth line define a fourth plane that is co-planar or parallel to the first plane. The first line and the fifth line intersect at an angle of 45 degrees when the fifth line is projected into the third plane. The fifth line and the sixth line define a fifth plane that is co-planar or parallel to the first plane. In some examples the third plane, the fourth plane and the fifth plane are parallel to each other but are not co-planar.

In another embodiment at least one of the first position marker, the second position marker, and the third position marker are embedded within the collection portion. In some examples the first position marker, the second position marker, and the third position marker are all embedded within the collection portion. It is possible that two of the first position marker, the second position marker, and the third position marker are on opposite surfaces of the collection portion.

In another embodiment the first position marker has a first color, the second position marker has a second color, the third position marker has a third color. Any one of the following is true: the first color, the second color and the third color are identical; the first color is different from the second color and the third color and the second color and the third color are the same; the first color is different from the second color and the third color and the second color is different from the third color; the first color is identical with the third color and the first color is different from the second color; the first color, the second color, and the third color all different; and the first color is identical with the second color and the first color is different from the third color.

In another embodiment the first position marker comprises any one of the following: a fluorescent dye, a luminescent dye, and an emissive electroluminescent compound.

In another embodiment the second position marker comprises any one of the following: a fluorescent dye, a luminescent dye, and an emissive electroluminescent compound.

In another embodiment the third position marker comprises any one of the following: a fluorescent dye, a luminescent dye, and an emissive electroluminescent compound.

An emissive electroluminescent compound is also commonly known as an OLED dye. An external optical system may activate the OLED or emissive electroluminescent compound externally to aid in defining the location of a particular position marker. The use of a fluorescent dye, a luminescent dye, and an emissive electroluminescent compound may assist in detecting and differentiating the position markers from each other. This may enable the markers to be detected independently from the primary detection method such as classical microscopy or laser scanning. This may have the advantage that the primary detection system can be optimized to the target cell or molecules and a secondary detection system can be optimized to detect the location of the position markers. This may enable a more accurate determination of the position and a more careful handling of a target cell or biological specimen.

In another embodiment at least one of the first position marker, the second position marker, and the third position marker comprises a magnetic marker or a radioactive marker. For instance a magnetic material may be embedded at the location of the first center point marker, the second center point marker, or the third center point marker. This may be used separately or in conjunction with a system for also identifying the location of the magnetic or radioactive center point markers.

As used herein in conjunction with optical analyzer systems, the term "color" refers to a wavelength or range of wavelengths of absorbed, transmitted or emitted electromagnetic radiation. In embodiments where a position marker comprises a magnetic marker, a "color" can refer to a characteristic of a magnetic marker that could be utilized to discriminate between magnetic markers. For example, the polarity or the direction of a magnetic field either from a permanent magnet or an energized electromagnet could be used to discriminate between different marker positions. Where the position markers are radioactive, a radiation detector could be employed, and, for example, where different radioactive markers are used for different position markers the characteristics of the radiation emitted by the different radioactive markers (such as alpha versus beta emission) can be used to discriminate between the different radioactive markers.

In another embodiment the collection portion comprises a microtiter plate.

In another embodiment the collection portion forms an orthogonal parallel pipette. Essentially the collection portion is a flat piece of glass or other transparent material which has the first, second and third position markers.

In another embodiment the collection portion is glass.

In another embodiment the collection portion is plastic.

In another embodiment the collection portion is a glass and plastic composite. The use of different materials such as glass or plastic may allow for surfaces receiving the biological sample to have different properties. For instance the particular plastic surface may be chosen such that it is hydrophilic or hydrophobic or may comprise other materials which help a cell to adhere to the surface.

In another embodiment the device is stackable with another copy of the device.

In another embodiment when closed the lid and the collection portion are spaced approximately one biological sample cell distance apart. For example plant and animal cells are typically between 10 µm and 100 µm in diameter.

In another embodiment when closed, the lid and the collection portion are spaced approximately one human blood cell distance apart. For instance a human erythrocyte or red blood cell is disc-shaped and has a diameter of approximately 6.2 to 8.2 µm. The red blood cell has a typical thickness of about 2 to 2.5 µm at its thickest point and its minimum thickness in the center is approximately 0.8 to 1 µm. The spacing between the surface of the collection portion and the lid and the surface for receiving the biological sample of the collection portion could be spaced such that it is slightly larger than either the large diameter or the height of the blood cell.

Another aspect provides for a system configured to perform optical analysis of a device according to an embodiment. The optical analyzer comprises a location identifier configured to automatically identify the location of the first location marker, the second location marker, and the third location marker. The optical analyzer is configured to identify the three-dimensional location of a biological element on the collection portion relative to the first location marker, the second location marker, and the third location marker. The optical analyzer may have an optical system for examining cells or other biological samples on the surface of the collection portion. This same optical inspection system may in some cases also be the location identifier. In other examples the location identifier may be separate from the optical inspection system. For instance an optical system optimized for locating the position of the first, second and third location markers may be used. Once the location of the first, second and third location markers is known then this can be used to calibrate the location on the surface of the collection portion.

In another embodiment the optical analyzer further comprises a memory for storing machine-executable instructions. The optical analyzer further comprises a processor for controlling the optical analyzer. Execution of the instructions causes the processor to identify the location of the first position marker, the second position marker, and the third position marker using the location identifier. Execution of the instructions further causes the processor to identify a biological element on the surface of the collection portion using the optical analyzer. The biological element may for instance be a biological sample or a cell. Execution of the instructions further causes the processor to extrapolate a three-dimensional position of the biological element using the location of the first position marker, the second position marker, and the third position marker. For instance inspection system of the optical analyzer may have a predefined relation to the location identifier. In this case it is a matter of straight forward extrapolation to determine the three-dimensional position of the biological element. This may enable repeatable determination of the coordinates of the biological element. This is particularly beneficial when the optical analyzer is moved to a different machine such as a machine for removing or extracting the biological element from the collection portion.

Another aspect provides for a method of identifying a three-dimensional location on a collection portion with a surface for receiving a biological sample. The surface defines a first plane; the collection portion is optically transparent. The collection portion comprises a first position marker. The first position marker indicates a first center point. The collection portion further comprises a second position marker. The second position marker indicates a second center point. The collection portion further comprises a third position marker. The third position marker indicates a third center point. The first center point, the second center point and the third center point define a second plane. The second plane and the first plane define a line of intersection. The method comprises identifying the location of the first position marker, the second position marker, and the third position marker using a location identifier. The method further comprises identifying a biological element on the surface of the collection portion. The method further comprises extrapolating the three-dimensional location of the biological element using the location of the first position marker, the second position marker, and the third position marker.

As will be appreciated by one skilled in the art, aspects of the present disclosure may be embodied as an apparatus, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present disclosure. Computer executable code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the subject matter. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

It is understood that one or more of the aforementioned embodiments of the subject matter may be combined as long as the combined embodiments are not mutually exclusive.

The following non-limiting examples illustrate certain embodiments of the present subject matter.

Examples

In the following, examples are provided in order to display certain embodiments and to exemplify the subject matter described herein. It is to be understood that also other embodiments are comprised by the scope of the subject matter, as known by the person skilled in the art.

FIG. 1 shows an example of the components which make up a device 100. The device 100 comprises a lid 102. The lid has a window 104 and a window holder 108.

The device 100 further comprises a collection portion support 110. The device 100 also comprises a collection portion 112. The collection portion has a surface 113 receiving a biological sample such as a cell.

The collection portion support 110 has a fluid inlet 114 at a first side 116 and a fluid outlet 118 at a second side 120. This provides a path for a fluid to flow through the device. This will be explained in greater detail in following Figs. On the side of the collection portion 112 there are a series of vents 122. These vents may be opened or closed to either seal the device or to enable the lid 102 to be removed more easily. The vent 122 is shown as having small stabilization elements 124 to stabilize the slits which make up the vents 122. The collection portion 112 can be placed into the collection portion support 110 and the lid 102 may be closed.

Figure 2:
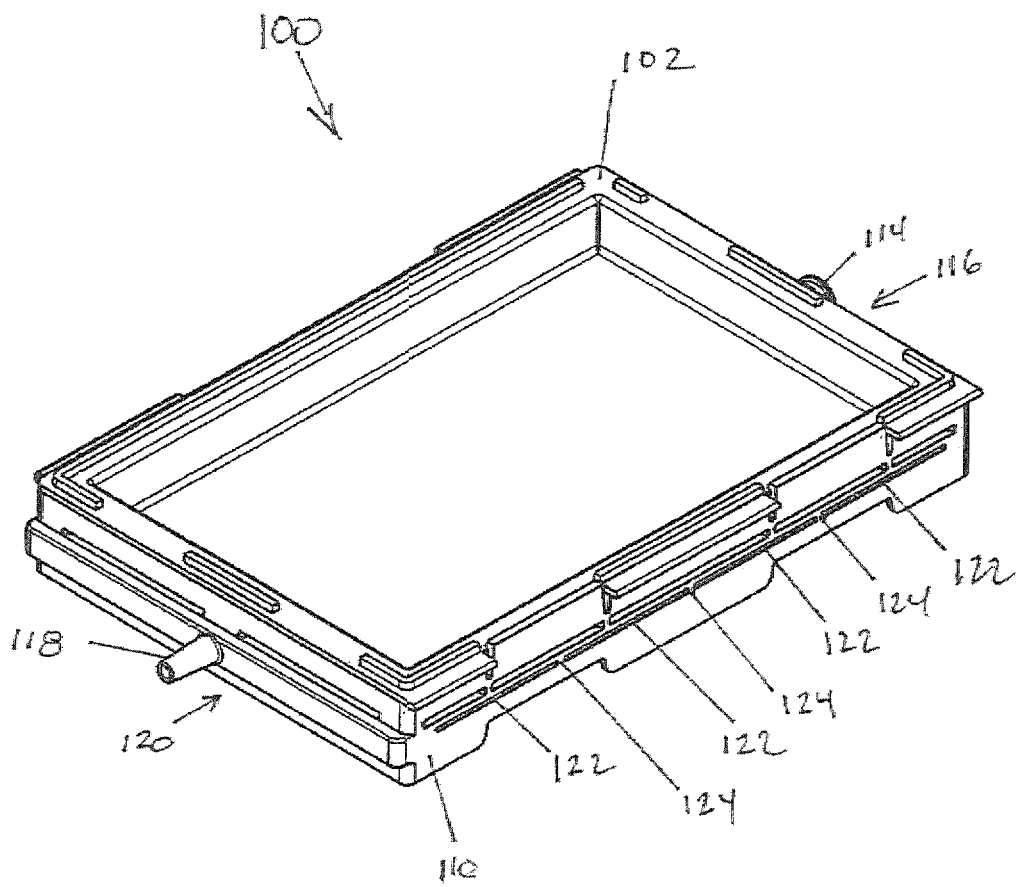
FIG. 2 shows perspective views of the components of the device when assembled.

FIG. 2 shows the device 100 after the lid 102, the collection portion support 110, and the collection portion 112 have been assembled.

Figure 3A:
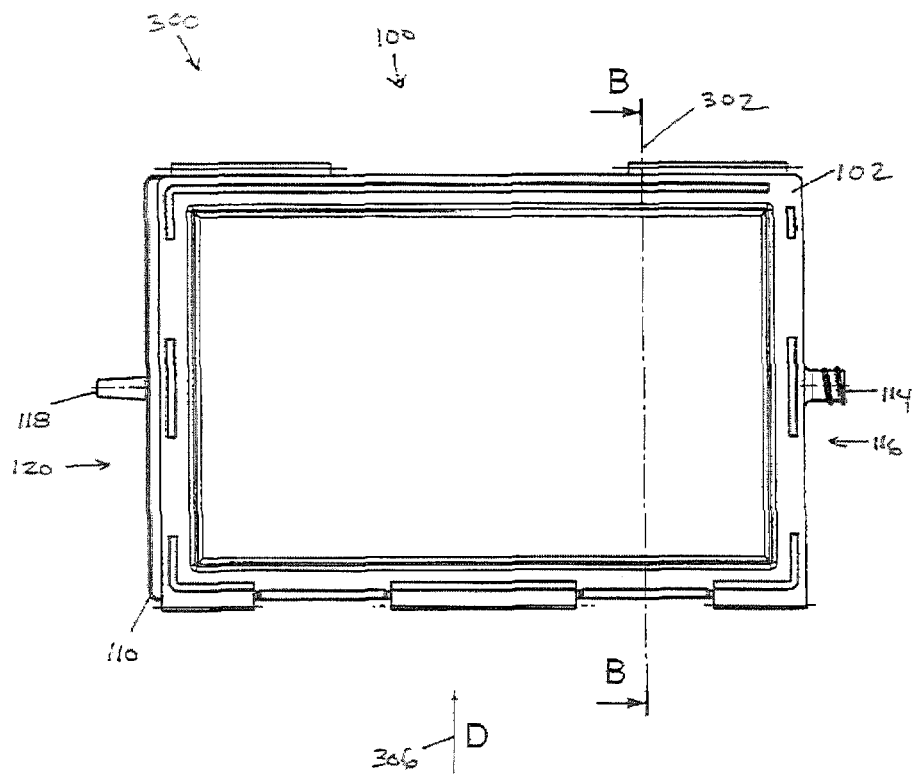
FIG. 3A shows a top view of the device.
Figure 3B:
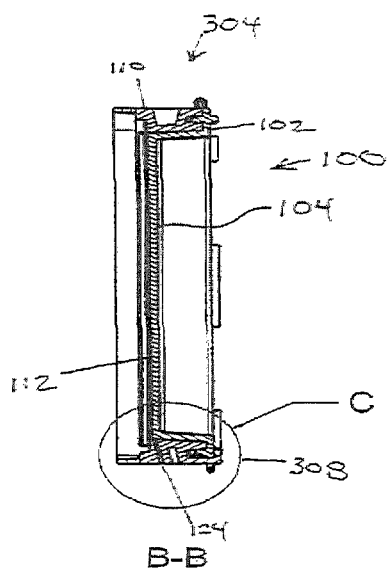
FIG. 3B shows a cross-sectional view of the device, taken along the line B-B in FIG. 3A.

FIG. 3A shows a top view 300 of the device 100. FIG. 3B shows a cross-sectional line 302 through the device 100 shown in view 300. This line 302 is also labeled B-B cross-section. Image 304 shows the cross-section along the line 302. There is an arrow labeled 306 and D, which points to a side of the top view 300. The arrow 306 indicates a side view which will be shown in a later Fig. The circle labeled 308 and also C shows a region which will be expanded in a later Fig. to show further details of the mechanical construction of the device 100.

Figure 4A:
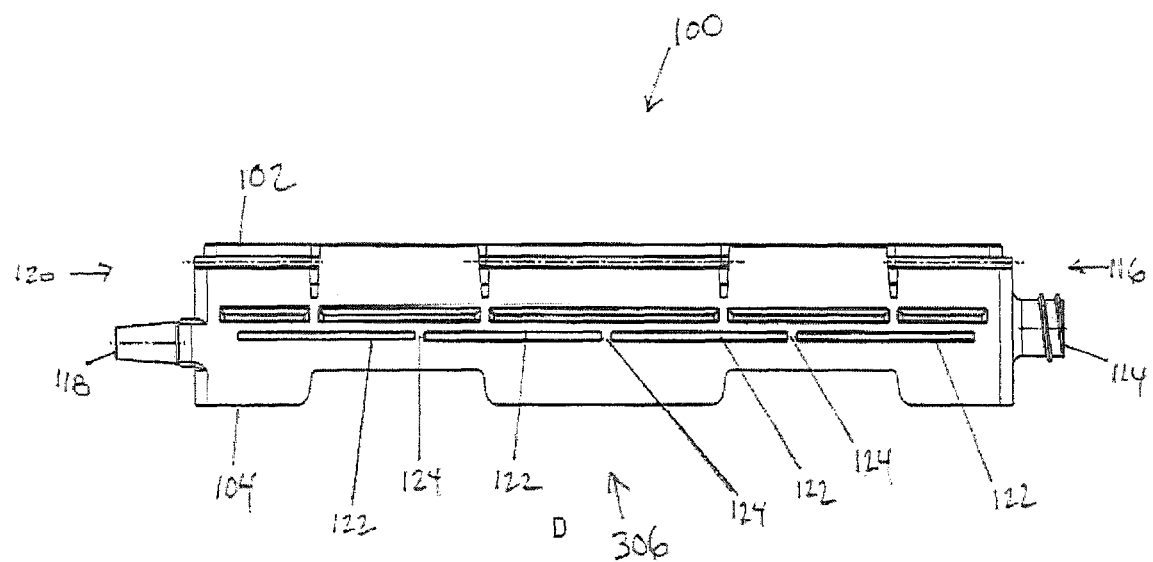
FIG. 4A show a side view of the device.

FIG. 4A shows the side view 306 of the device 100. The side view 306 shows the vents 122 in greater detail. The fluid inlet 114 can be seen at the first side 116 and the fluid outlet 118 can be seen at the second side 120.

Figure 4B:
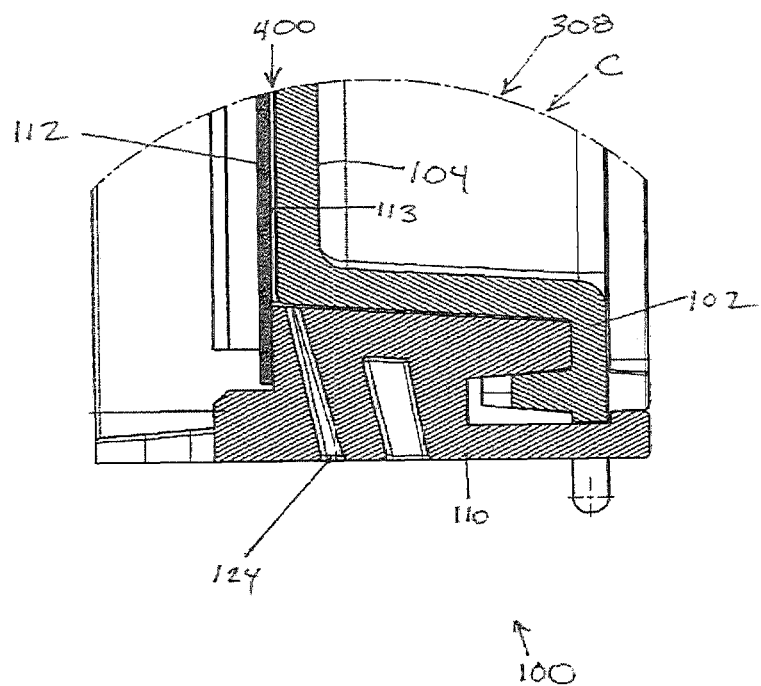
FIG. 4B shows a detail view of the cross-section of area C in FIG. 3B.

FIG. 4B shows the portion 308 of the cross-sectional view labeled 308 or C. The assembly of the lid 102, the collection portion support 110 and the collection portion 112 can be seen in greater detail. In particular it can be seen how the collection portion 112 and the window 104 define an interior volume 400. The interior volume for instance could be filled with cells or other biological elements or samples. The vent 124 is shown as providing a vent directly to the interior volume 400. Also the surface 113 is shown as forming a portion of the interior volume 400. In this example the window 104 and the lid 102 are formed from a single piece. In other examples the window 104 could be a separate piece which is attached to the lid 102. The vent 124 accesses the interior volume 400. The lid 102 and the collection portion support 110 also have a surface which forms a portion of the interior volume 400.

Figure 5:
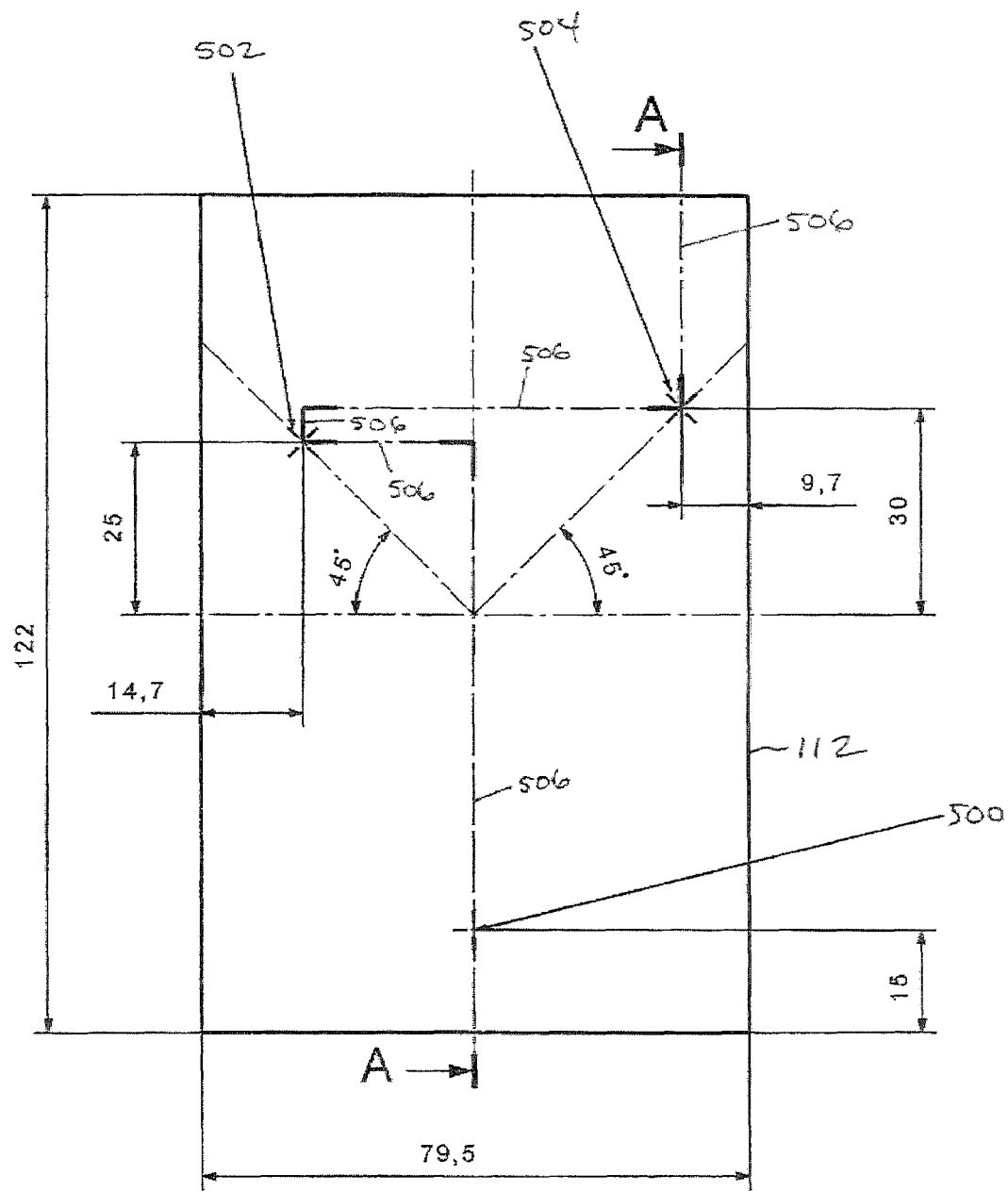
FIG. 5 shows a schematic diagram of a collection portion of the device.

FIG. 5 shows an example of a collection portion 112. The collection portion in FIG. 5 shows the first position marker 500, the second position marker 502, and the third position marker 504. All of the position markers shown in this Fig. have a point-like center point marker with two line-like linear indicators for each center point marker. The linear indicators help a machine-readable system to identify the location of the center point markers. Dimensions for this collection portion 112 are given in millimeters. The dimensions and exact positions of the position markers 500, 502, 504 are purely exemplary. The position markers 500, 502 and 504 are shown as having their linear indicators as being rotated relative to one another. There is a cross-sectional line 506 or A-A that snakes through the collection portion 112. The cross-sectional view will be shown in FIG. 6A.

Figure 6A:
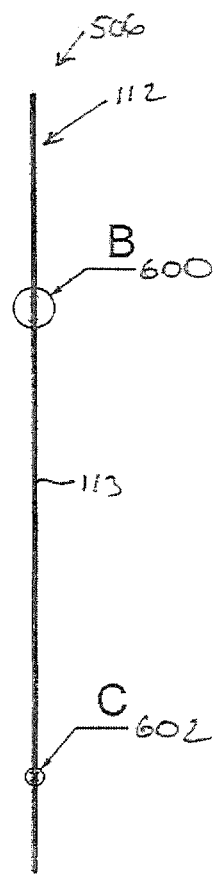
FIG. 6A show a cross-sectional view of the collection portion of the device, taken along the line A-A in FIG. 5.
Figure 6B:
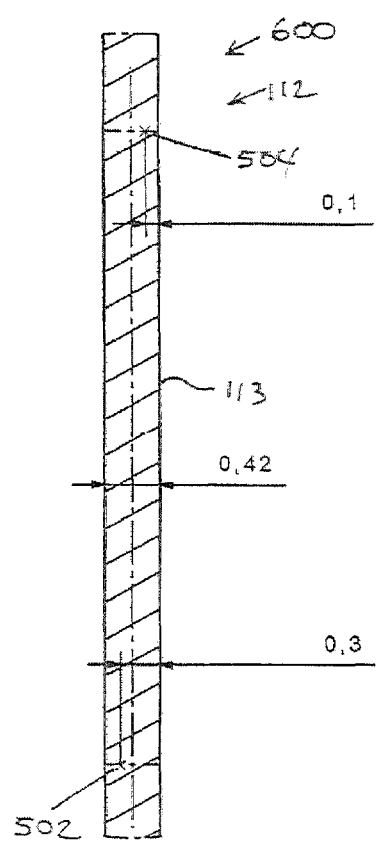
FIG. 6B shows a detail view of the cross-section of area B in FIG. 6B.
Figure 6C:
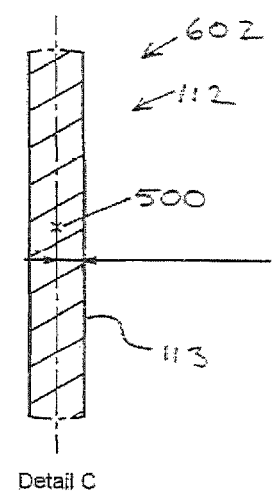
FIG. 6C shows a detail view of the cross-section of area C in FIG. 6A.

FIG. 6A shows the cross-sectional view 506 of the collection portion 112. In this cross-sectional view 506 there are two regions which are expanded. The region labeled B or 600 and the region labeled C or 602. Image 600 contains the position of the cross-sectional view labeled B or 600. Within this cross-sectional view the third position marker 504 and the second position marker 502 can be seen. Likewise, image 602 shows the expanded view of the cross-sectional view region labeled C or 602. Within image 602 the position of the first position marker 500 can be seen. It can be seen that in this particular example all three position markers 500, 502, 504 are embedded within the collection portion 112. In alternative examples one of two of the position markers could be on a surface of the collection portion.

Figure 7A:
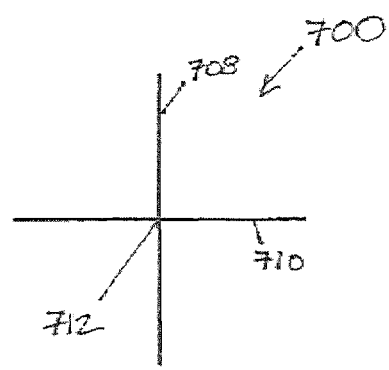
FIGS. 7Aa, 7Ab, 7Ac, 7Ad, 7Ba, 7Bb, 7Ca, 7Cb, and 7Cc show schematic diagrams of examples of position markers.
Figure 7A:
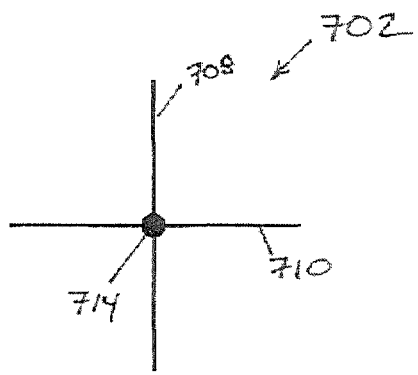
Figure 7A:
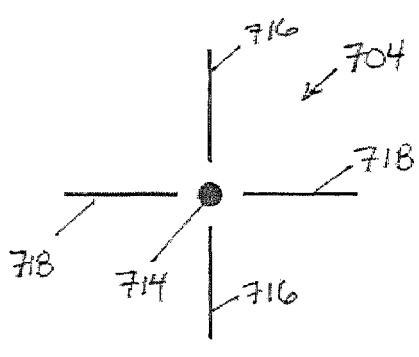
Figure 7A:
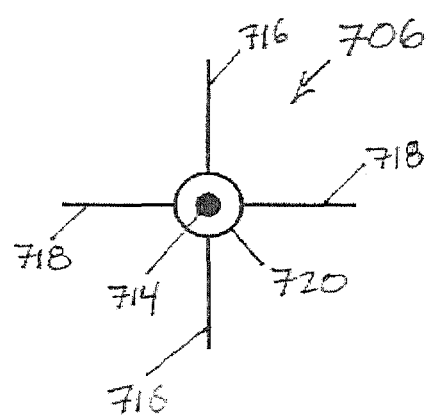

FIGS. 7Aa through Ad, 7Ba and 7Bb, and 7Ca through Cc show several examples of position markers. In FIG. 7Aa through 7Ad four cross shaped position markers 700, 702, 704, 706 are shown. Position marker 700 comprises a first linear indicator 708 and a second linear indicator 710 that intersect a center point 712. The first linear indicator 708 and the second linear indicator 710 are shown as intersecting at an angle of 90 degrees. However, it is possible for the linear indicators 708 and 710 to intersect at an angle other than 90 degrees, such as any angle between 1 and 90 degrees, but for automatic or machine recognition of the center point of the position marker it is computationally advantageous to use an angle of intersection of 90 degrees.

Position marker 702 is similar to the position marker 700. Position marker 702 comprises a first linear indicator 708 and a second linear indicator 710 that intersect a center point. The center point in this example is indicated by a center point indicator 714. The center point indicator is a solid circular dot. The first linear indicator 708 and the second linear indicator are shown as intersecting at an angle of 90 degrees.

Position marker 704 is similar to the position marker 702, however the linear indicators 716, 718 are discontinuous in the region of the center point indicator 714. Linear indicator 716 comprises two line segments and linear indicator 718 also comprises two line segments. The first linear indicator 716 and the second linear indicator 718 are shown as intersecting at an angle of 90 degrees. However, it is possible for the linear indicators 716 and 718 to intersect at an angle other than 90 degrees, such as any angle between 1 and 90 degrees, but for automatic or machine recognition of the center point of the position marker it is computationally advantageous to use an angle of intersection of 90 degrees.

The position marker 704 may have several advantages. These may include one or more of the following:

The location of the center point is computationally efficient to determine.

The clear 90° angle between linear indicators 716 and 718 aids the determination of the center point.

The linear indicators 716 and 718 define a two-dimensional plane.

The center point marker 714 is easy to identify.

The gap between the center point marker 714 and the linear indicators 716 and 718 has a defined space (which may be useful for size calculation of cell, cell compartments, etc.).

The plane of the cross defined by 716 and 718 is parallel to the surface plane of the glass plate. In case the glass plate is not exactly perpendicular to the optical view, the "arms" are optically shorter. By calculating with a triangulation the deviation of the perpendicularity (in 3D) from the ideal situation can be determined.

The use of different colors for different position markers may enable the identification of an individual point.

When using three of these position markers each of the three crosses defined by 716 and 718 may be rotated with an angle of 45° which may enable more accurate calculation of the position.

A more complicated design of the position marker may obscure details of objects on the collection portion. In many situations the position marker 704 provides a good balance between identifying spatial relations and visibility of materials deposited on the collection portion.

The position marker 706 is similar to the position marker 704, however the position marker 706 additionally comprises a first circular center point indicator 720. The first circular center point indicator 720 is an unfilled circle centered about the center point to be indicated.

Figure 7B:
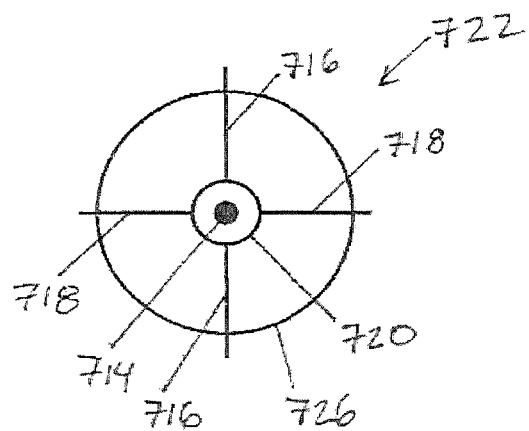
Figure 7B:
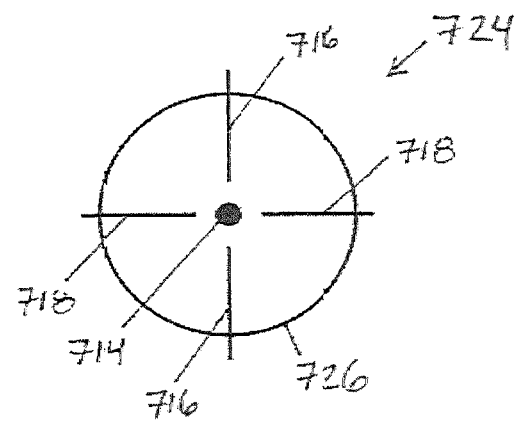

FIGS. 7Ba and 7Bb show two additional examples of position markers 722, 724. The position markers 722 and 724 show two possible cross and circular position markers.

The position marker 722 is similar to the position marker 706, however position marker 722 additionally has a second circular center point indicator 726. The second circular center point indicator 726 is an unfilled circle center about the center point to be indicated. The second circular center point indicator 726 has a larger radius than the first center point indicator 720.

The position marker 724 is similar to the position marker 704, however the position marker 722 additional has the second circular center point indicator 726 that is present in marker 722. Position marker 724 could also be considered to be similar to position marker 706, with the radius of 720 being increased.

Figure 7C:
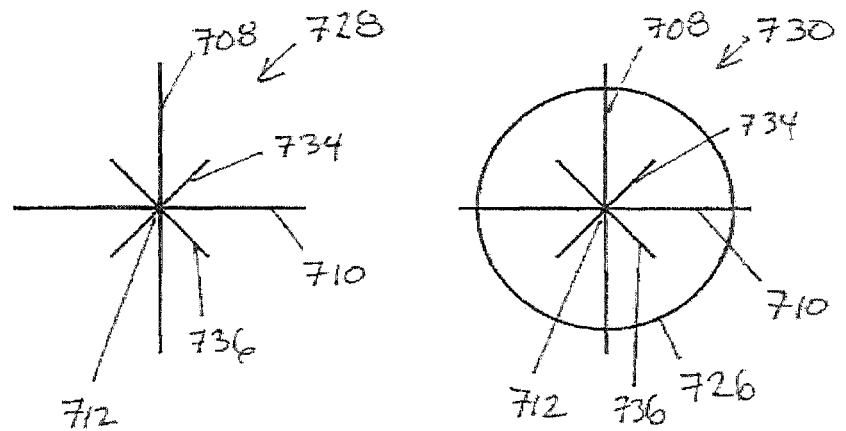
Figure 7C:
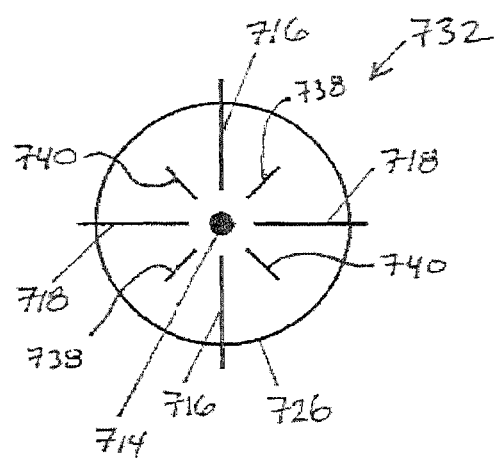

FIG. 7Ca through 7Cc show three additional examples of position markers 728, 730, 732. The position markers 728, 730, and 732 combine two cross shaped markers.

The position marker 728 is similar to the position marker 700, however the position marker 728 contains two additional linear indicators 734, 736. Position marker 728 comprises a third linear indicator 734 and a fourth linear indicator 736. The third linear indicator 734 and the fourth linear indicator intersect at the center point 712. The third linear indicator 734 and the fourth linear indicator 736 are shown as intersecting at an angle of 90 degrees. However, it is possible for the linear indicators 734 and 736 to intersect at an angle other than 90 degrees, such as any angle between 1 and 90 degrees, but for automatic or machine recognition of the center point of the position marker it is computationally advantageous to use an angle of intersection of 90 degrees.

The third linear indicator 734 and the fourth linear indicator 736 form a cross that is rotated 45 degrees with respect to the cross formed by the first linear indicator 708 and the second linear indicator 710. However, it is possible for the cross formed by the third linear indicator 734 and the fourth linear indicator 736 to be rotated by a different angle with respect to the cross formed by the first linear indicator 708 and the second linear indicator 710. For example, this rotation could be any angle between 1 and 90 degrees. For automatic or machine recognition of the center point of the position marker it is computationally advantageous to use an angle of rotation of 45 degrees.

The position marker 730 is similar to the position marker 728, however the position marker 730 additionally has the second circular center point indicator 726 that is present in marker 722.

The position marker 732 is similar to the position marker 724, however the position marker 732 contains two additional linear indicators 738, 740. Position marker 732 comprises a third linear indicator 738 and a fourth linear indicator 738.

The linear indicators 738, 740 are discontinuous in the region of the center point indicator 714. The third linear indicator 734 and the fourth linear indicator intersect at the center point 712. The third linear indicator 738 comprises two line segments and the fourth linear indicator 740 also comprises two line segments.

The third linear indicator 738 and the fourth linear indicator 740 are shown as intersecting at an angle of 90 degrees. However, it is possible for the linear indicators 738 and 740 to intersect at an angle other than 90 degrees, such as any angle between 1 and 90 degrees, but for automatic or machine recognition of the center point of the position marker it is computationally advantageous to use an angle of intersection of 90 degrees.

The third linear indicator 738 and the fourth linear indicator 740 form a cross that is rotated 45 degrees with respect to the cross formed by the first linear indicator 716 and the second linear indicator 718. However, it is possible for the cross formed by the third linear indicator 738 and the fourth linear indicator 740 to be rotated by a different angle with respect to the cross formed by the first linear indicator 716 and the second linear indicator 718. For example, this rotation could be any angle between 1 and 90 degrees. For automatic or machine recognition of the center point of the position marker it is computationally advantageous to use an angle of rotation of 45 degrees.

Figure 8:
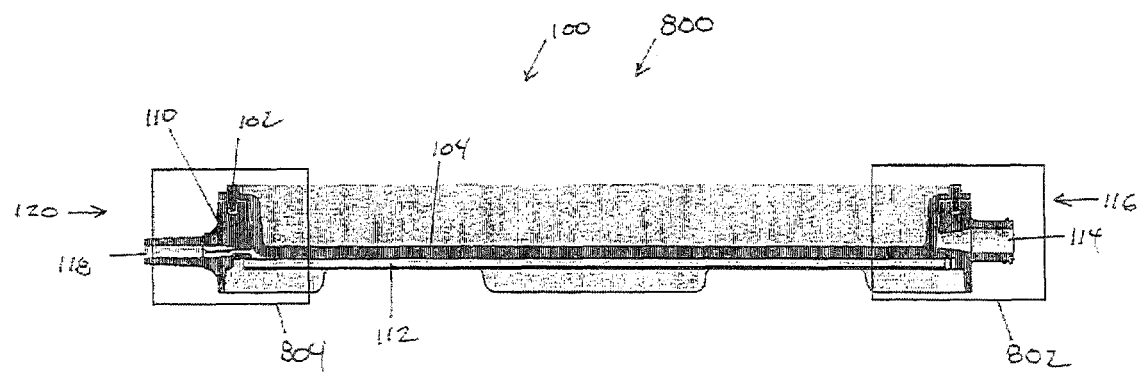
FIG. 8 shows a cross-sectional view of the device as shown in FIG. 2.

FIG. 8 shows a cross-sectional view 800 of the device 100. The cross-sectional view passes directly through the center of the fluid inlet 114 and the fluid outlet 118. In the cross-sectional view 800 there is a region labeled 802 which will be expanded in a further Fig. There is a second region 804 which will be expanded in a different Fig.

Figure 9:
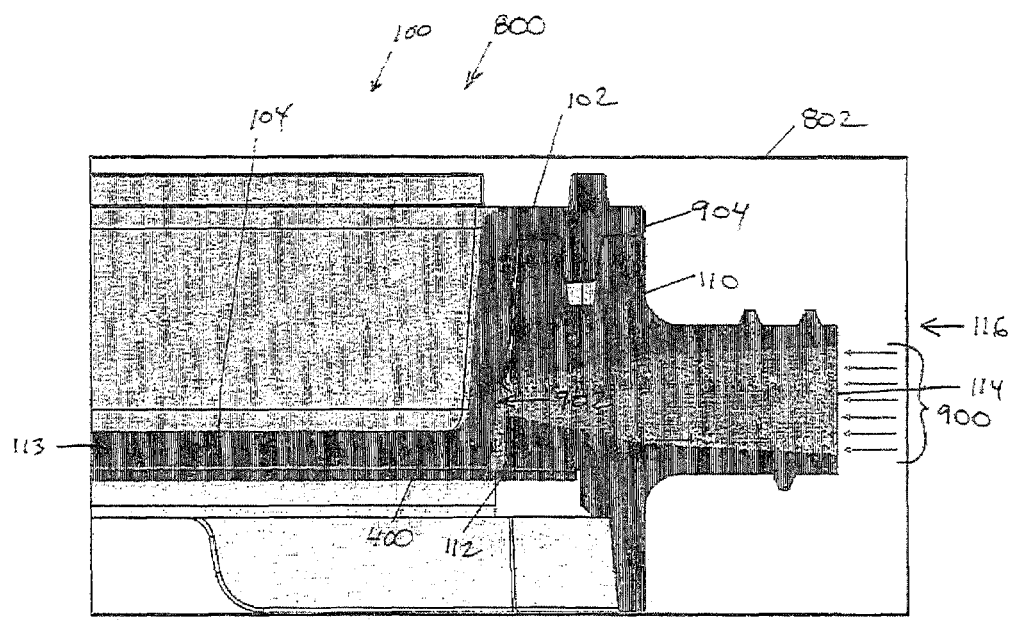
FIG. 9 shows a detail view of region 802 in FIG. 8.

FIG. 9 shows the region 802 of the cross-sectional view 800 of the device 100. The arrows 900 indicate fluid flow into fluid inlet 114. The fluid flows into the inlet 114 and the fluid comes in contact with the surface labeled 902. This surface forces the fluid 900 to abruptly change direction before entering the interior volume 400. This helps to more evenly distribute the fluid 900 and control the fluid flow more evenly in the interior volume 400. The region labeled 904 is a sealing surface between the lid 102 and the collection portion support.

Figure 10:
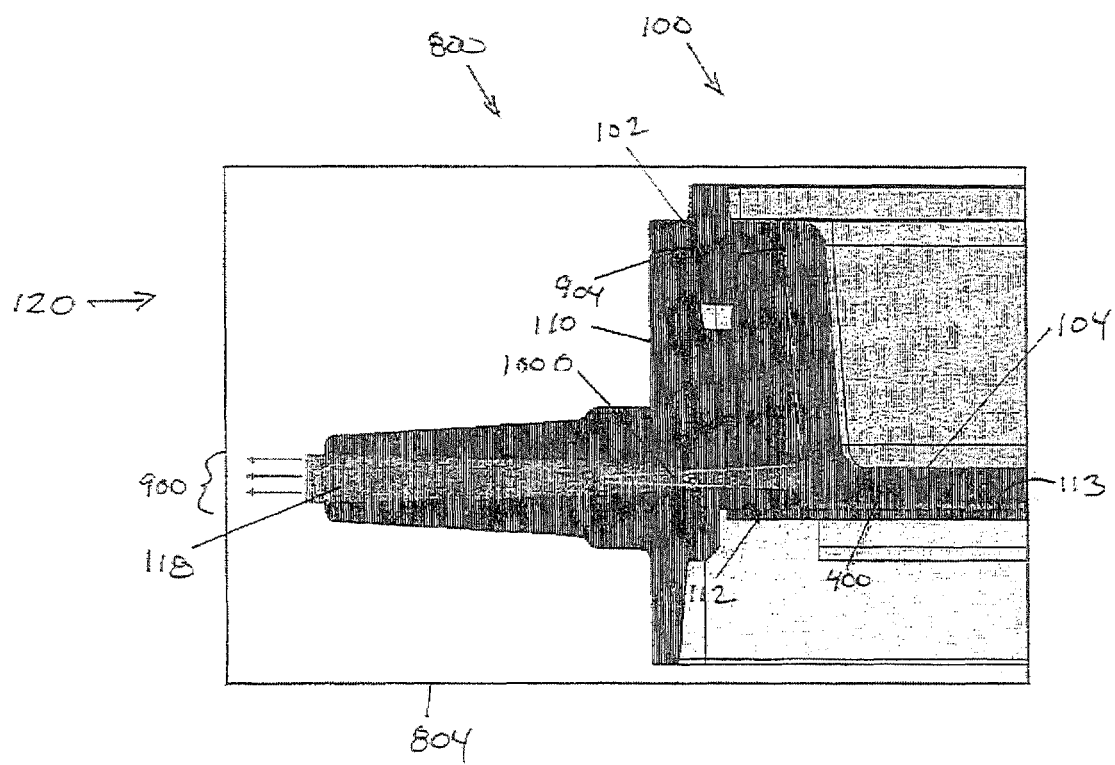
FIG. 10 shows a detail view of region 804 in FIG. 8.

FIG. 10 shows the enlarged region 804. In 804 an enlarged portion of the cross-sectional view 800 of the device 100 is shown. In this view it can be seen that the interior volume is drained by a slit 100 that runs the length of the collection portion 112. The slit 100 then allows the fluid to be channeled to the fluid outlet 118. The arrows labeled 900 shows the path of the fluid flow. The region labeled 904 in this view is again a sealing surface 904 between the lid 102 and the collection portion support 110.

Figure 11:
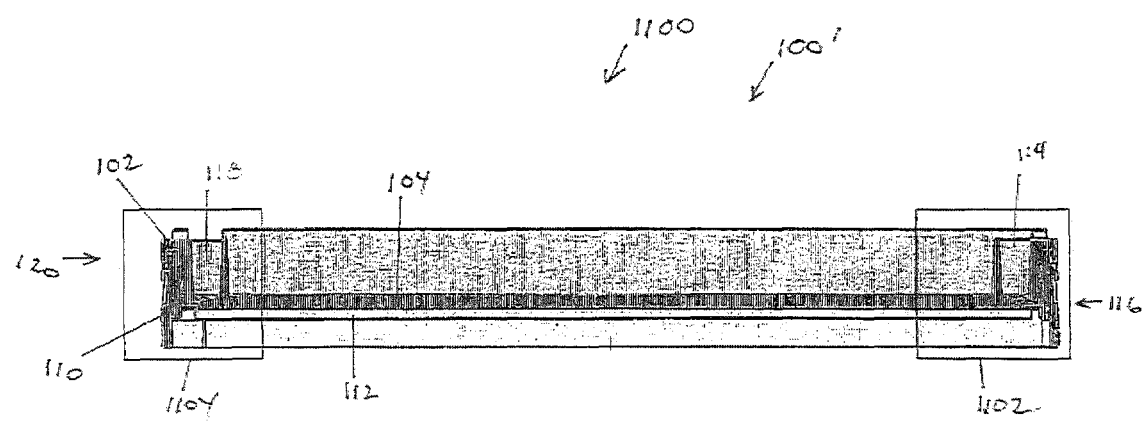
FIG. 11 shows a cross-sectional view of another exemplary embodiment of the device.

FIG. 11 shows an alternative example of a device 100'. The device 100' is similar to that of device 100 shown in previous Figs. except the fluid inlet 114 and the fluid outlet 118 are in the lid 102 instead of in the collection portion support 110. The cross-sectional view 1100 passes through the center of both the fluid inlet 114 and the fluid outlet 118. The box 1102 indicates a region that will be expanded in a following Fig. The region 1104 indicated by a box will also be expanded in a following Fig.

Figure 12:
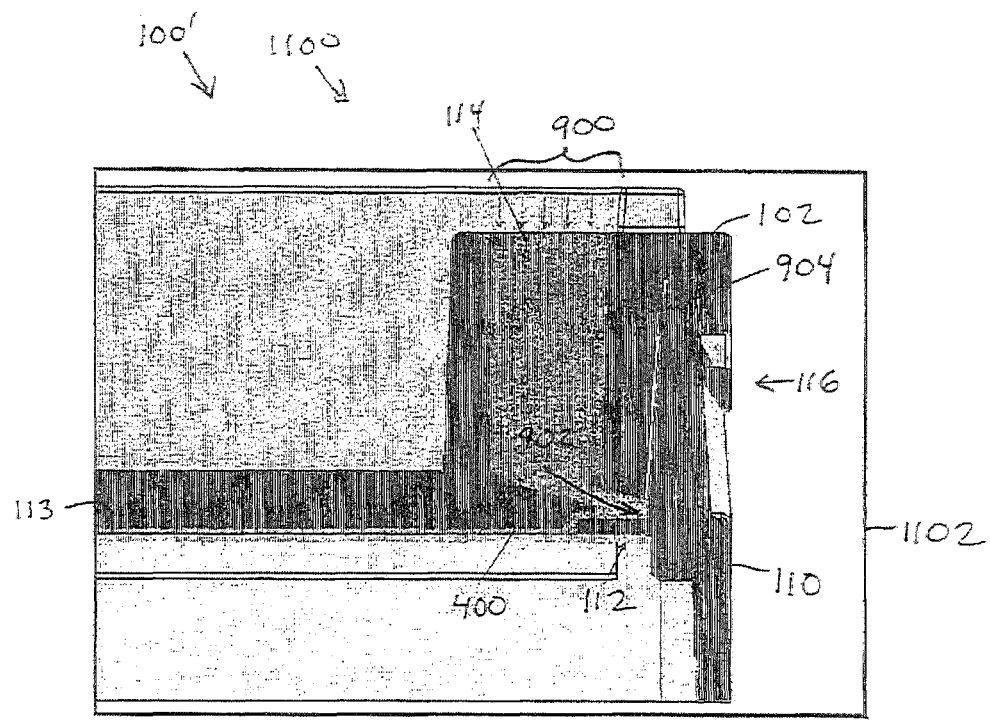
FIG. 12 shows a detail view of region 1102 in FIG. 11.

FIG. 12 shows the expanded region 1102 of the cross-sectional view 1100. The fluid inlet 114 has arrows 900 indicating the path of fluid flow. The fluid flows into the fluid inlet 114 and then contacts a surface 902 of the collection portion support 110. There is a slit that runs the length of the glass plate 112 and forcing the fluid 900 against the surface 902 changes the direction of the fluid flow and helps to distribute it even as it flows through the interior volume 400. The region 904 is a sealing surface between the lid 102 and the collection portion support 110.

Figure 13:
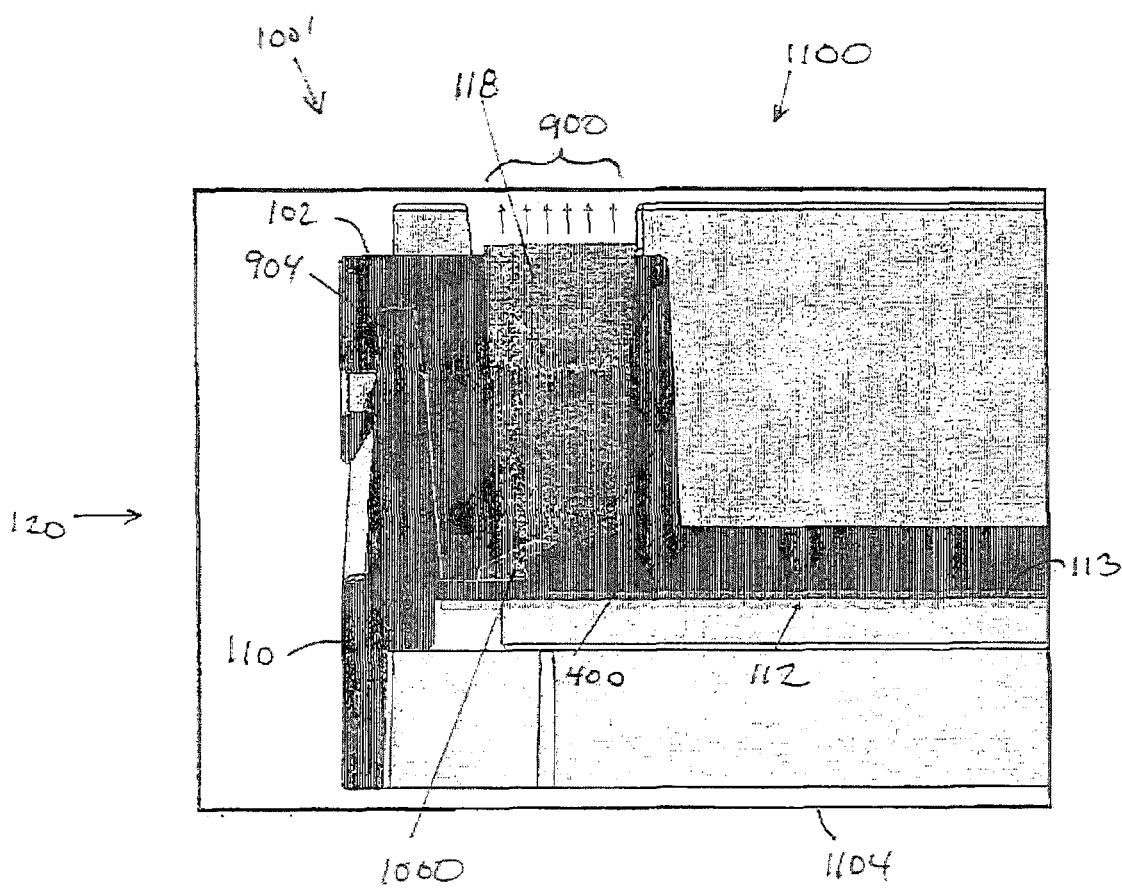
FIG. 13 shows a detail view of region 1104 in FIG. 11.

FIG. 13 shows the region 1104 of the cross-sectional view 1100. The arrows 900 again indicate the fluid flow out of the fluid outlet 118. The interior volume 400 connects with a slit 1000 that runs the length of the collection portion 112. The slit 1000 then opens into the fluid outlet 118. The slit 1000 helps to keep the fluid flow across the entire surface of the collection portion 112 uniform.

Figure 14:
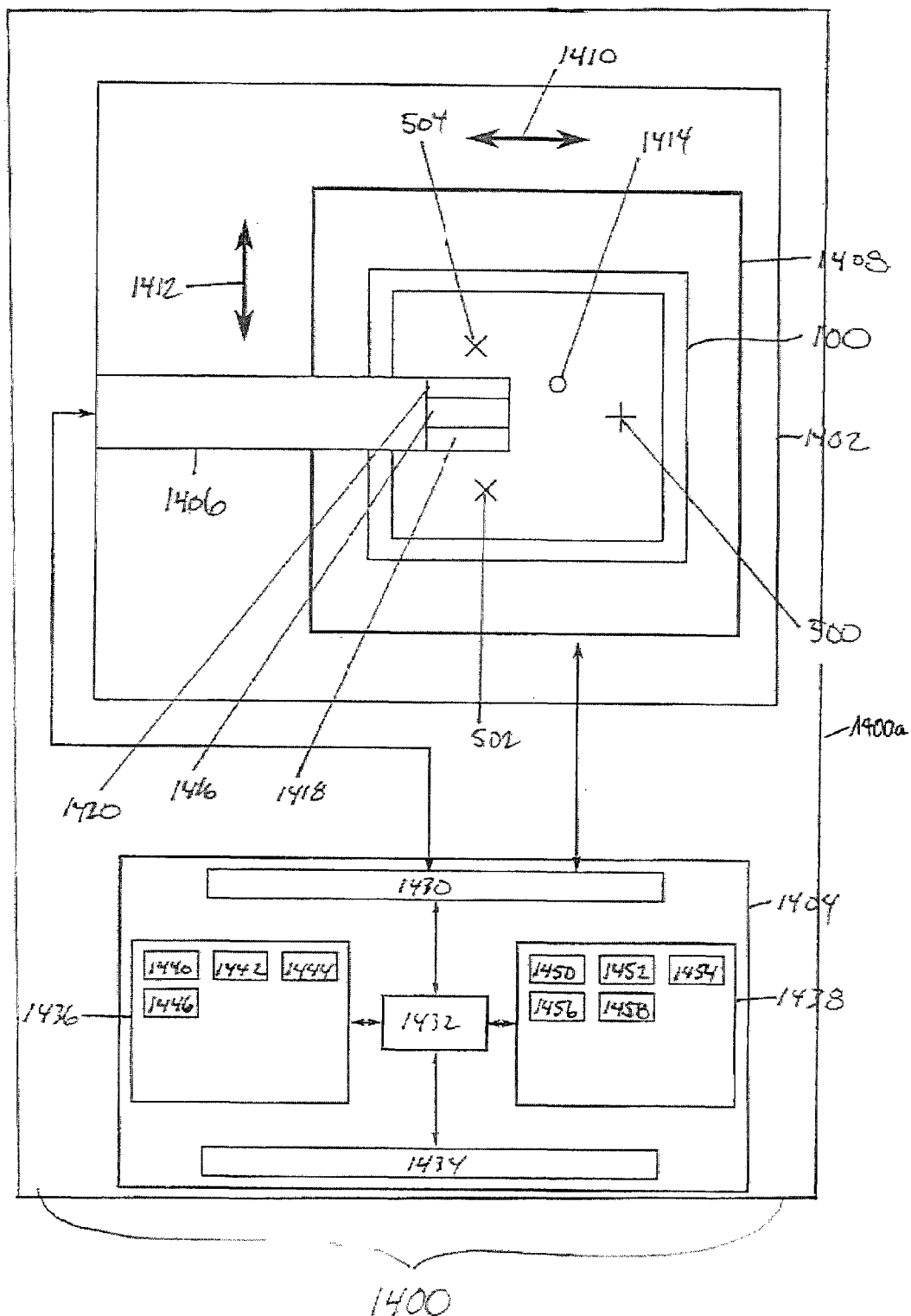
FIG. 14 shows a schematic diagram of an example of an optical analyzer.

FIG. 14 illustrates an example of a system 1400. The system 1400 comprises an apparatus 1402 and a computer 1404 for controlling the operation and function of the apparatus 1402. In one embodiment, the computer 1404 and apparatus 1402 are integrated in a single optical analyzer instrument 1400a, In this embodiment, the system (1400) comprises the optical analyzer (1400a). The apparatus 1402 is shown in functional terms and shown from above. There is a pedestal 1406 which is suspended above a translation table 1408. The translation table 1408 is able to move in the x-direction 1410 and the y-direction 1412. The translation table 1408 may also be able to move in a z-direction which is perpendicular to both the x 1410 and the y 1412 directions. There is a collection portion 100 mounted on the translation table 1408. The translation table 1408 moves the collection portion 100 under the pedestal 1406. At a distal end of the pedestal 1406 there is an optical inspection system 1416, a location identifier 1418, and in some examples a cell extraction apparatus 1420. In some examples the optical inspection system 1416 and the location identifier 1418 are the same pieces of equipment.

The location identifier 1418 is able to identify the center point location of a first position marker 500, a second position marker 502, and a third position marker 504 that are located in the collection portion 100. The optical inspection system 1416 is able to scan cells or other biological elements within the interior volume of the collection portion to locate specific cell types. For instance in this Fig. a biological cell 1414 is shown. After identifying the location of the position markers 500, 502, 504 the system 1400 can interpolate the position of the biological cell 1414. For instance the optical inspection system may identify the biological cell 1414 as being of interest and then determine its position on the collection portion. In some examples the lid from the device 100 can be removed and then the cell extraction apparatus 1420 can remove or capture the biological cell 1414. For instance a pipetting-type apparatus could be used to extract the biological cell 1414.

The instruments 1416, 1418, 1420 that are on pedestal 1406 are connected to a hardware interface 1430 of computer 1404. The translation table 1408 is also connected to the hardware interface 1430. The hardware interface 1430 is connected to a process 1432 and a computer 1404. The hardware interface 1430 enables the process 1432 to exchange data with and to control the components of the apparatus 1402. The processor 1432 is shown as being further connected with a user interface 1434, computer storage 1436, and computer memory 1438.

The computer storage 1436 is shown as containing a calibration location measurement 1440. The calibration location measurement 1440 comprises data acquired by the location identifier 1418 to identify the location of the position markers 500, 502, 504. The computer storage 1436 is further shown as containing optical data 1442 acquired using the optical inspection system 1416. The computer storage 1436 is shown as containing a cell location measurement which was acquired during the acquisition of the optical data 1442. The computer storage 1436 is further shown as containing cell location coordinates 1446 that were computed using the cell location measurement 1444 and the calibration location measurement 1440. This could for example be done by a prior knowledge of the position of the position markers 500, 502, 504 in combination with the calibration location measurement 1440.

The computer memory 1438 is shown as containing a control module 1450. The control module 1450 comprises computer-executable code which enables the processor 1432 to control the operation and function of the apparatus 1402. The computer memory 1438 is further shown as containing a location identifier control module 1452. The location identifier control module 1452 comprises computer-executable code which enables the processor 1432 to acquire the calibration location measurement 1440 using the location identifier 1418. The computer memory 1438 is further shown as containing a coordinate interpolation module 1454. The coordinate interpolation module 1454 contains computer-executable code which enables the determination of the cell location coordinates 1446 from the calibration location measurement 1440 and the cell location measurement 1444. The coordinate interpolation module 1454 may also comprise data which holds the geometric relation between the position markers 500, 502, 504.

The computer memory 1438 further contains a pattern recognition module 1456 for analyzing the contents of the optical data 1442 to determine or identify the biological cell 1414. There may also be data which was acquired during the acquisition of the optical data 1442 such as the cumulative movement of the translation table 1408 or the like, such that the coordinates of the biological cell 1414 relative to the collection portion may be determined. The computer memory 1438 optionally contains a cell extraction control module 1458 which contains computer code which enables the processor 1432 to control the apparatus 1402 to extract the biological cell 1414 with the cell extraction apparatus 1420. The cell extraction control module 1458 may for instance use the location identifier control module 1452 to relocate the position markers 500, 502, 504 to re-determine the cell location coordinates 1446 prior to extracting the cell 1414.

Figure 15:
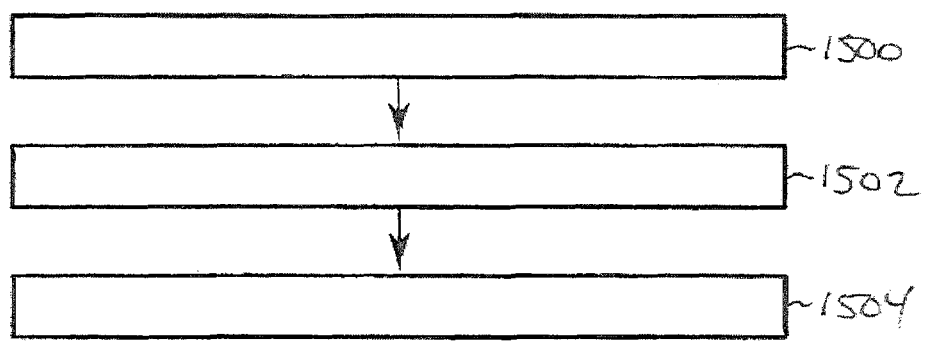
FIG. 15 shows a flowchart which illustrates a method.

FIG. 15 shows a flowchart which illustrates a method. Step 1500 comprises identifying the location of a first position marker 500; a second position marker 502 and a third position marker 504 in three-dimensional space of a location identifier according to an example previously given. This method is performed using a collection portion with a surface for receiving a biological sample. The surface defines a first plane. The collection portion comprises the first position marker, which has a first center point marker. The collection portion further comprises a second position marker, which has or comprises a second center point marker. The collection portion further comprises a third position marker which comprises a third center point marker. The center point markers identify a particular location in three-dimensional space. The first center point, the second center point, the third center point define a second plane. The second plane and the first plane define a line of intersection. The method further comprises the step of identifying a biological element on the surface of the collection portion. Finally in step 1504 the method comprises extrapolating the three-dimensional location of the biological element using the location of the first position marker, the second position marker, and the third position marker.

LIST OF REFERENCE NUMERALS

- 100 device
- 100' device
- 102 lid
- 104 window
- 108 window holder
- 110 collection portion support
- 112 collection portion
- 113 surface
- 114 fluid inlet
- 116 first side
- 118 fluid outlet
- 120 second side
- 122 vent
- 124 stabilization element
- 300 top view of 100
- 302 section line
- 304 cross sectional view along 302
- 306 indication of side view
- 308 portion of cross sectional view
- 400 interior volume
- 500 first position marker
- 502 second position marker
- 504 third position marker
- 506 cross section line
- 600 portion of cross sectional view 506
- 602 portion of cross sectional view 602
- 700 position marker
- 702 position marker
- 704 position marker
- 706 position marker
- 708 first linear indicator
- 710 second linear indicator
- 714 center point indicator
- 716 first linear indicator
- 718 second linear indicator
- 720 first circular center point indicator
- 722 position marker
- 724 position marker
- 726 second circular center point indicator
- 728 position marker
- 730 position marker
- 732 position marker
- 734 third linear indicator
- 736 fourth linear indicator
- 738 third linear indicator
- 740 fourth linear indicator
- 800 cross sectional view
- 802 portion of cross sectional view 800
- 804 portion of cross sectional view 800
- 900 fluid flow
- 902 surface
- 904 sealing surface
- 1000 slit for draining fluid
- 1100 cross section view
- 1102 portion of cross sectional view 1100
- 1104 portion of cross sectional view 1100
- 1400 system
- 1400a optical analyzer instrument
- 1402 apparatus
- 1404 computer
- 1406 pedestal
- 1408 translation table
- 1410 x-direction
- 1412 y-direction
- 1414 biological cell
- 1416 optical inspection system
- 1418 location identifier
- 1420 cell extraction apparatus
- 1430 hardware interface
- 1432 processor
- 1434 user interface
- 1436 computer storage
- 1438 computer memory
- 1440 calibration location measurement
- 1442 optical data
- 1444 cell location measurement
- 1446 cell location coordinates
- 1450 control module
- 1452 location identifier control module
- 1454 coordinate interpolation module
- 1456 pattern recognition module
- 1458 cell extraction control module While the foregoing embodiments have been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of identifying a three-dimensional location on a device for collection of biological samples, the device comprising a lid, a collection portion support, and a collection portion with a surface for receiving a biological sample; wherein the lid comprises a window and a window holder; wherein the surface defines a first plane; wherein the collection portion comprises a first position marker; wherein the first position marker indicates a first center point; wherein the collection portion further comprises a second position marker; wherein the second position marker indicates a second center point; wherein the collection portion further comprises a third position marker; wherein the third position marker indicates a third center point; wherein the first center point, the second center point, and the third center point define a second plane; wherein the second plane and the first plane define a line of intersection; wherein the device has an interior volume defined partially by the collection portion support, the collection portion, the window, and the window holder; wherein the interior volume has interior surfaces; wherein the window is operable to allow inspection of the first position marker, the second position marker, and the third position marker; wherein the method comprises:

identifying, through the window of the device, the location of the first position marker, the second position marker, and the third position marker using a location identifier;

identifying a biological element on the surface of the collection portion;

extrapolating the three-dimensional location of the biological element using the location of the first position marker, the second position marker, and the third position marker.

2. The method of claim 1, wherein the first position marker further comprises a first linear indicator, wherein the first linear indicator defines a first line through the first center point, wherein the first position marker comprises a second linear indicator, wherein the second linear indicator defines a second line through the first center point, wherein the first line and the second line are perpendicular, wherein the second position marker comprises a third linear indicator, wherein the third linear indicator defines a third line through the second center point, wherein the second position marker comprises a fourth linear indicator, wherein the fourth linear indicator defines a fourth line through the second center point, wherein the third line and the fourth line are perpendicular, wherein the third position marker further comprises a fifth linear indicator, wherein the fifth linear indicator defines a fifth line through the third center point, wherein the third position marker comprises a sixth linear indicator, wherein the sixth linear indicator defines a sixth line through the third center point, and wherein the fifth line and the sixth line are perpendicular.

3. The method of claim 2, wherein the first, second, third, fourth, fifth, and sixth linear indicators are discontinuous in the region of the center point indicators and comprise two line segments.

4. The method of claim 2, wherein the first line and the second line define a third plane that is co-planar or parallel to the first plane, wherein the first line and the third line intersect at an angle of 45 degrees when the third line is projected onto the third plane, wherein the third line and the fourth line define a fourth plane that is co-planar or parallel to the first plane, wherein the first line and the fifth line intersect at an angle of 45 degrees when the fifth line is projected onto the third plane, and wherein the fifth line and the sixth line define a fifth plane that is co-planar or parallel to the first plane.

5. The method of claim 1, wherein at least one of the first position marker, the second position marker, and the third position marker are embedded within the collection portion.

6. The method of claim 1, wherein the first position marker has a first color, wherein the second position marker has a second color, wherein the third position marker has a third color, and wherein any one of the following: the first color, the second color, and the third color are all identical; the first color, second color and third color are all different from each other; the first color is different from the second color and the third color and the second color and the third color are the same; the first color is identical with the third color and the first color is different from the second color; and the first color is identical with the second color and the first color is different from the third color.

7. The method of claim 1, wherein the first position marker comprises any one of the following: a fluorescent dye, a luminescent dye, an emissive electroluminescent compound and/or the second position marker comprises any one of the following: a fluorescent dye, a luminescent dye, an emissive electroluminescent compound and/or the third position marker comprises any one of the following: a fluorescent dye, a luminescent dye, an emissive electroluminescent compound.

8. The method of claim 1, wherein at least one of the first position marker, the second position marker, and the third position marker comprises a magnetic marker.

* * * * *